(12) United States Patent
Polka

(10) Patent No.: US 10,688,008 B2
(45) Date of Patent: Jun. 23, 2020

(54) PHYSICAL THERAPY SYSTEM

(71) Applicant: One80 Physical Therapy, P.C., Loveland, CO (US)

(72) Inventor: Rhett E. Polka, Loveland, CO (US)

(73) Assignee: One80 Physical Therapy, P.C., Loveland, CO (US)

( * ) Notice: Subject to any disclaimer, the term of this patent is extended or adjusted under 35 U.S.C. 154(b) by 488 days.

(21) Appl. No.: 14/242,592

(22) Filed: Apr. 1, 2014

(65) Prior Publication Data
US 2015/0272498 A1 Oct. 1, 2015

(51) Int. Cl.
*A61H 1/02* (2006.01)
*A61B 5/11* (2006.01)
(Continued)

(52) U.S. Cl.
CPC .............. *A61H 1/02* (2013.01); *A61B 5/1104* (2013.01); *A61B 5/45* (2013.01); *A61B 5/4519* (2013.01);
(Continued)

(58) Field of Classification Search
CPC .......... A61H 1/00; A61H 99/00; A61H 1/008; A61H 1/02; A61H 7/00; A61H 7/001; A61H 7/002; A61H 7/003; A61H 7/007; A61H 15/00; A61H 23/00; A61H 2201/16; A61H 2201/1657; A61H 2201/1683; A61H 2201/169; A61H 2201/1692; A61H 2201/1695; A61H 2201/5053; A61H 2203/0443; A61H 2203/0456; A61H 2203/0468; A61H 2203/0475; A61H 2205/06; A61H 2205/08; A61H 2205/10; A61H 2205/106; A61H 2205/108; A61B 5/4519; A61B 5/45
(Continued)

(56) References Cited

U.S. PATENT DOCUMENTS 4,452,237 A * 6/1984 Lewis ..................... A61H 39/04
601/134
5,501,657 A * 3/1996 Feero ........................ A61H 7/00
128/898

(Continued)

OTHER PUBLICATIONS

Schneider et. al., "Manual Medicine Therapy", Thime Medical Publishers 1988, pp. 8, 10, 13 and 104-105.*
(Continued)

*Primary Examiner* — Colin W Stuart
(74) *Attorney, Agent, or Firm* — Craig R. Miles; CR Miles P.C.

(57) ABSTRACT

A method for stimulating contraction of a target muscle, the method including: locating a first neuromuscular junction of a target muscle by visualization or palpation, delivering a first stimulus to the first neuromuscular junction, locating a second neuromuscular junction of the target muscle by visualization or palpation, and delivering a second stimulus to the second neuromuscular junction. The first and second stimuli are effective to stimulate contraction of the target muscle. Further, contraction of the target muscle is effective to result in a measurable increase of at least one of: output force of the target muscle or range of motion of a body part associated with extension or contraction of the target muscle.

15 Claims, 13 Drawing Sheets

(51) Int. Cl.
  *A61B 5/00* (2006.01)
  *A61H 99/00* (2006.01)
  *A61H 1/00* (2006.01)
(52) U.S. Cl.
  CPC ............... *A61H 1/00* (2013.01); *A61H 99/00* (2013.01); *A61H 2205/06* (2013.01); *A61H 2205/08* (2013.01); *A61H 2205/10* (2013.01); *A61H 2205/106* (2013.01); *A61H 2205/108* (2013.01)
(58) Field of Classification Search
  USPC ........................................................ 601/134
  See application file for complete search history.

(56) References Cited

U.S. PATENT DOCUMENTS

| | | | | |
|---|---|---|---|---|
| 5,674,261 | A * | 10/1997 | Smith | A61N 1/322 607/148 |
| 6,267,738 | B1 * | 7/2001 | Louis | A61H 1/008 601/118 |
| 6,821,260 | B2 * | 11/2004 | Fors | A61H 7/00 601/115 |
| 2003/0199792 | A1 * | 10/2003 | Austin | A61H 39/04 601/1 |
| 2005/0075590 | A1 * | 4/2005 | Filippi | A61H 1/008 601/107 |
| 2007/0233211 | A1 * | 10/2007 | Galer | A61F 7/007 607/96 |
| 2007/0270727 | A1 * | 11/2007 | Khorassani Zadeh | A61H 1/008 601/120 |
| 2008/0004554 | A1 * | 1/2008 | Smith | A61H 7/001 601/134 |
| 2009/0156968 | A1 * | 6/2009 | Sheradha | A61H 23/06 601/1 |
| 2010/0185259 | A1 * | 7/2010 | Shiba | A61H 39/002 607/48 |
| 2010/0256722 | A1 * | 10/2010 | Chu | A61N 1/0452 607/145 |
| 2012/0245410 | A1 | 9/2012 | Davis | |
| 2013/0096467 | A1 * | 4/2013 | Jacobs | A61H 99/00 601/1 |
| 2014/0257152 | A1 * | 9/2014 | Sandell | A61H 99/00 601/134 |
| 2014/0288471 | A1 * | 9/2014 | Gangwish | A61H 39/00 601/46 |

OTHER PUBLICATIONS

Mary Beth Braun, et. al., Introduction to Massage Therapy: Ch. 11: Therapeutic Applications (Lippincott Williams & Wilkins, 2008).*
Waybackmachine. Action Potential Physical Therapy—Home Page; captured Jun. 27, 2009. Website, https://web.archive.org, originally downloaded May 3, 2018, 2 pages.
U.S. Appl. No. 13/986,447, filed May 2, 2013, Jou.
U.S. Appl. No. 13/986,447; Appeal 2019-003305, Decision on Appeal mailed Jun. 17, 2019, 16 pages.
Definition of MAT. W. B. Saunders Co., Philadelphia, PA, 2002; Clinical Kinesiology, Beardall, Lake Grove, OR, 1985, 4 pages.
Waybackmachine. MAT: Muscle Activation Techniques—Home Page; captured Sep. 24, 2001. Website, https://web.archive.org, originally downloaded Jan. 28, 2020, 3 pages.

* cited by examiner

PHYSICAL THERAPY SYSTEM

FIELD OF THE INVENTION

A physical therapy system including a method useful in increasing muscle control or decreasing neuromuscular inhibition of a target muscle.

II. BACKGROUND OF THE INVENTION

Conventional physical therapy may be used to aid a subject having impaired muscle control, which may include general manipulation of the muscle to increase muscle relaxation. Typically, a provider may work with a subject to determine limitations in muscle control by assessing muscle length and gross strength. Subsequently, the provider may provide the subject with a preferred set of exercises targeted toward increasing gross strength of the impaired muscle. This approach may focus on alleviating symptoms of pain, swelling, tightness, or the like, as opposed to focusing on the underlying cause of these symptoms to restore normal physiologic function and biomechanics of muscle control.

The underlying cause of symptoms related to impaired muscle control such as pain, swelling, tightness, or the like, may be neuromuscular inhibition resulting from an incomplete or complete inhibition of neuromuscular transmission. Generally, neuromuscular transmission occurs at a neuromuscular junction, where neurotransmitters can be released from a prejunctional nerve ending, traverse a synapse, and bind to receptors on a postjunctional muscle membrane. Overall, the neuromuscular transmission signaling cascade can result in the transfer of an action potential from a motor neuron to a muscle fiber, resulting in muscle contraction. However, when the function of one or more components of the neuromuscular transmission signaling cascade is compromised, neuromuscular transmission may be either partially or completely inhibited.

Because conventional methods focus on alleviating symptoms of impaired muscle control and may not focus on modulating neuromuscular transmission, there would be an advantage in an inventive method which acts to increase muscle control or modulate the neuromuscular transmission signaling cascade to decrease neuromuscular inhibition, which in turn can act to increase muscle control.

III. SUMMARY OF THE INVENTION

Accordingly, a broad object of the invention can be to provide a physical therapy system which includes methods useful in increasing muscle control of a target muscle.

Another broad object of the invention can be to provide a physical therapy system which includes methods useful in decreasing neuromuscular inhibition of a target muscle.

Another broad object of the invention can be to provide a physical therapy system which includes methods useful in increasing neuromuscular transmission of a target muscle.

Another broad object of the invention can be to provide a physical therapy system which includes methods useful in stimulating contraction of a target muscle.

Another broad object of the invention can be to provide a physical therapy system which includes methods useful in alleviating one or more symptoms associated with loss of muscle control.

Another broad object of the invention can be to provide a physical therapy system which includes methods useful in alleviating symptoms including pain, swelling, tightness, or the like, or combinations thereof.

Another broad object of the invention can be to provide a physical therapy system which includes methods useful in increasing the output force of a target muscle.

Another broad object of the invention can be to provide a physical therapy system which includes methods useful in increasing the range of motion of a body part associated with extension or contraction of a target muscle.

Another broad object of the invention can be to provide a physical therapy system which includes methods useful in restoring normal physiologic function, biomechanics, or the like, or combinations thereof.

Naturally, further objects of the invention are disclosed throughout other areas of the specification, drawings, and claims.

IV. BRIEF DESCRIPTION OF THE DRAWINGS

FIG. 1 provides a flow diagram of a method included in a particular embodiment of the inventive physical therapy system.

Figure 11:
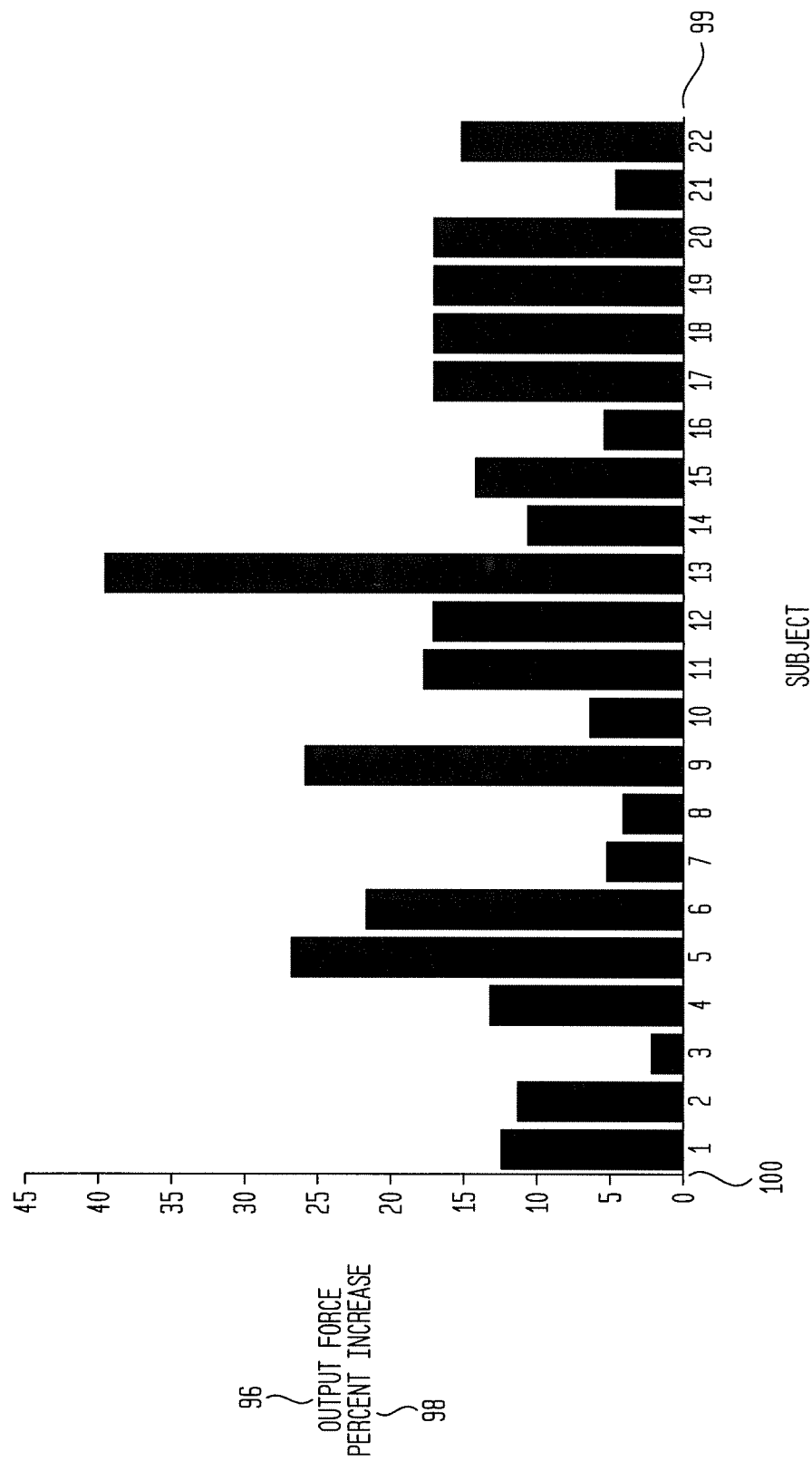

FIG. 11 provides a graph illustrating the percent increase in rectus femoris muscle output force following administration of a method included in a particular embodiment of the inventive physical therapy system.

Figure 12:
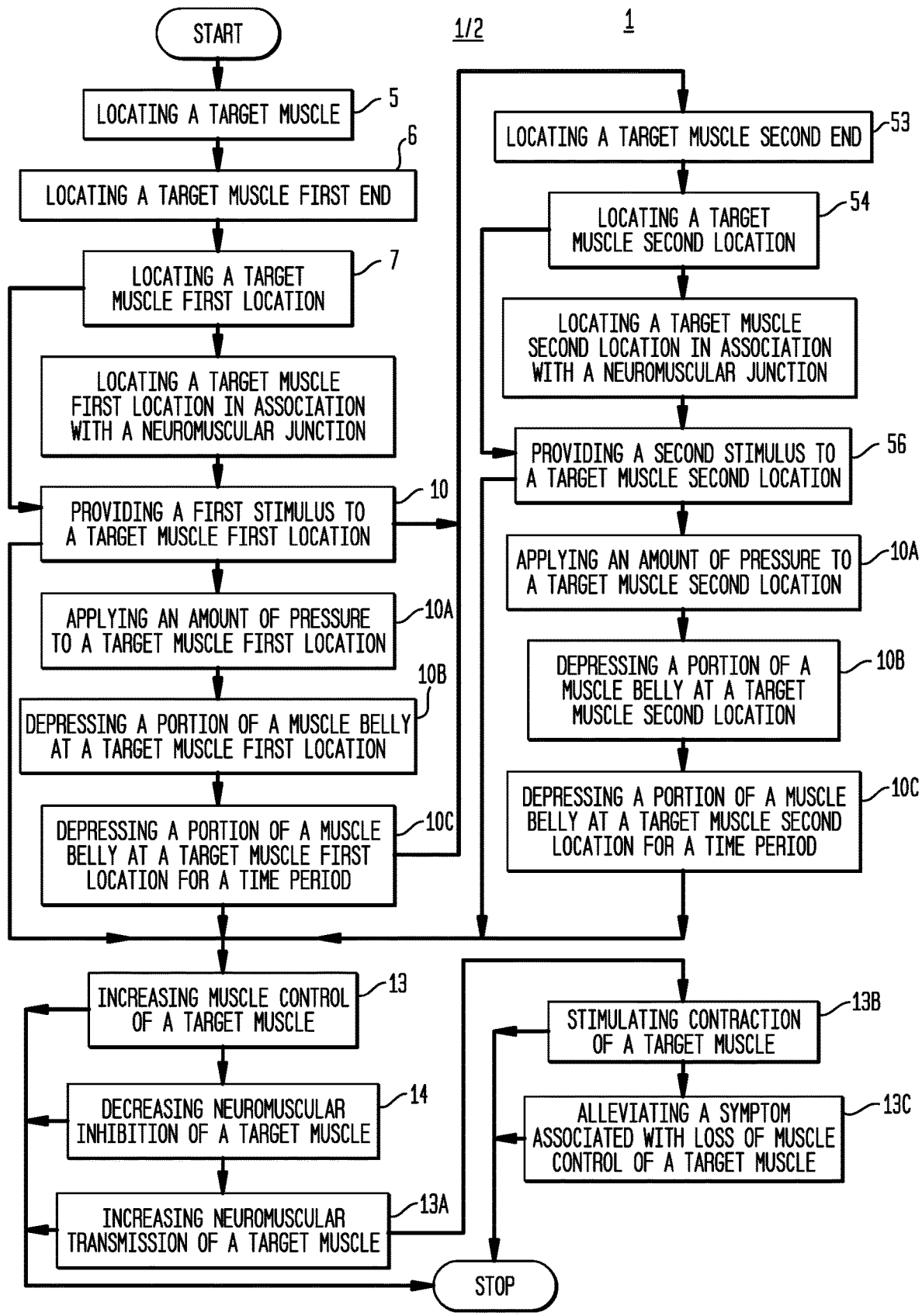

FIG. 12 provides a flow diagram of a method included in a particular embodiment of the inventive physical therapy system.

Figure 13:
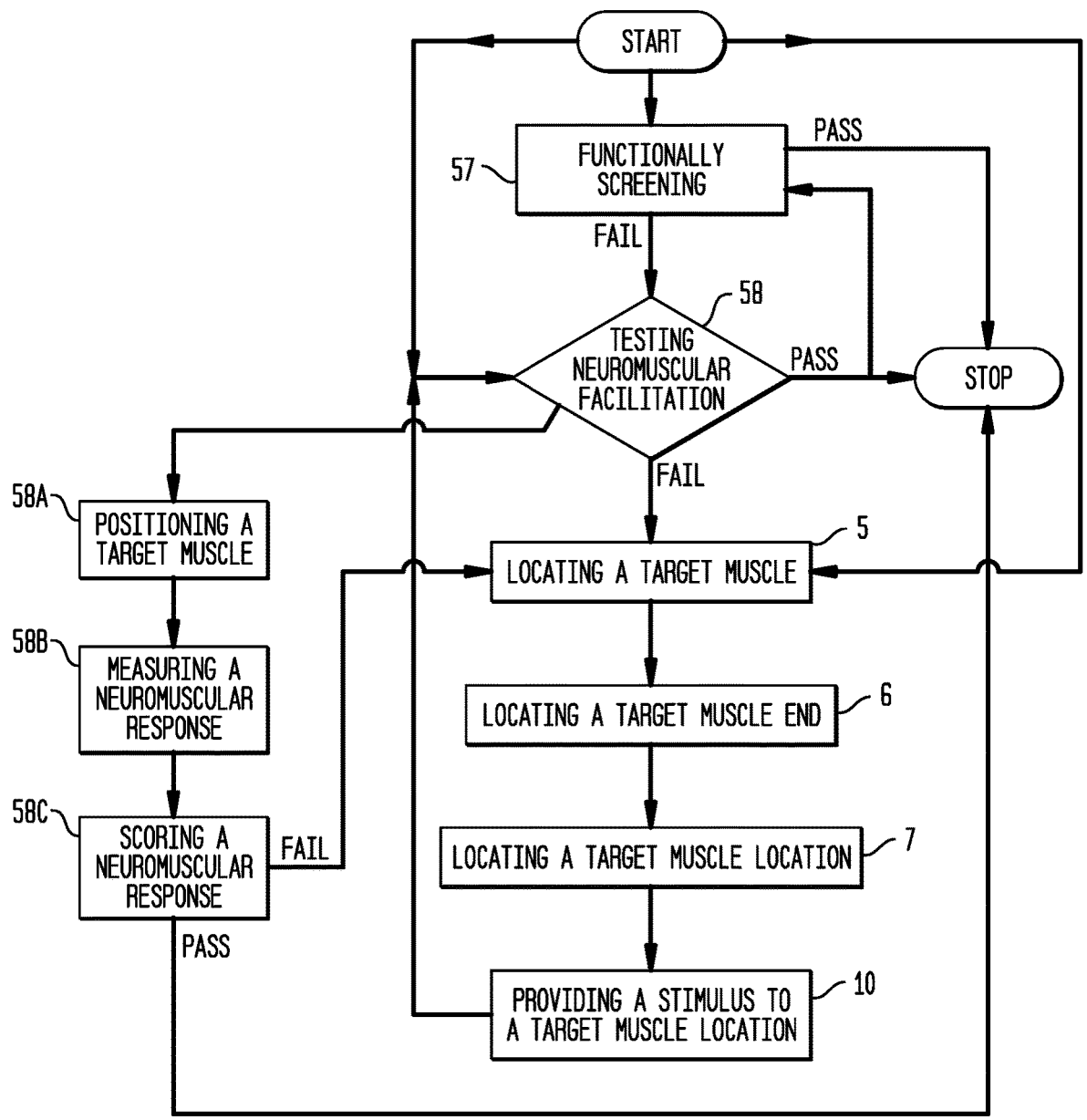

FIG. 13 provides a flow diagram of a method included in a particular embodiment of the inventive physical therapy system.

V. DETAILED DESCRIPTION OF THE INVENTION

Now referring generally to FIG. 1 through FIG. 13, which illustrate an inventive physical therapy method (1) useful in increasing muscle control, which can result from decreasing neuromuscular inhibition of a target muscle (3) of a subject (4).

Figure 1:
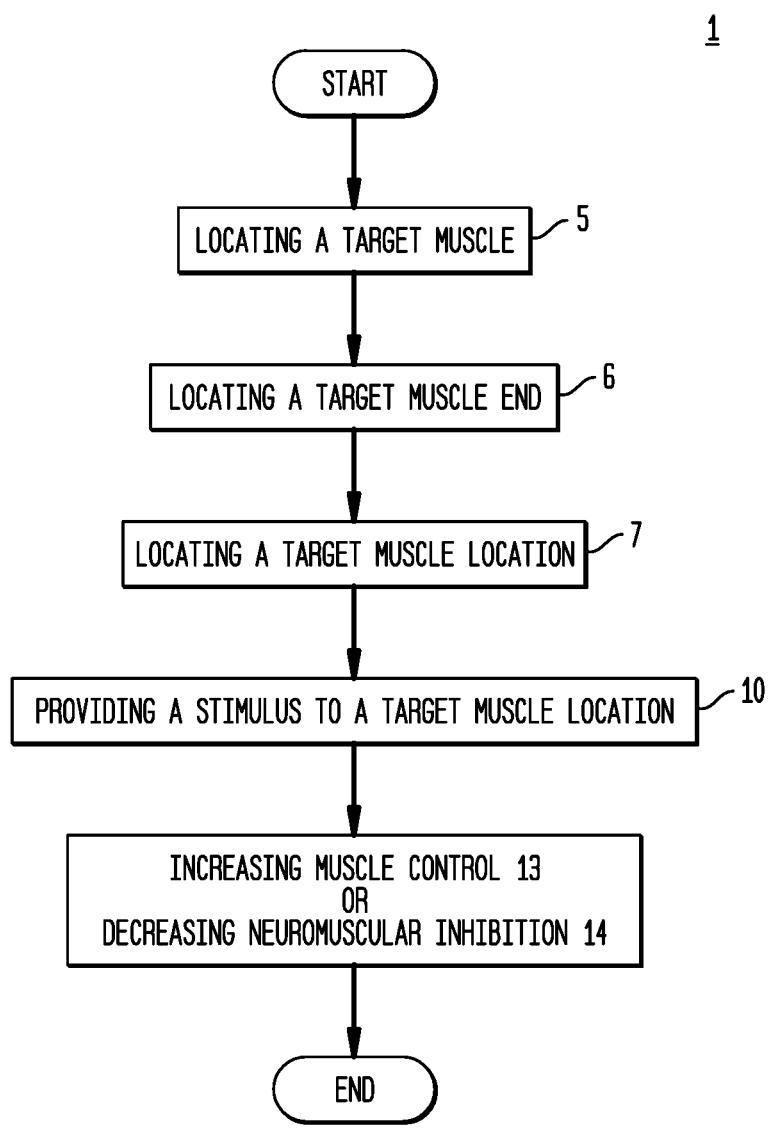
Figure 2:
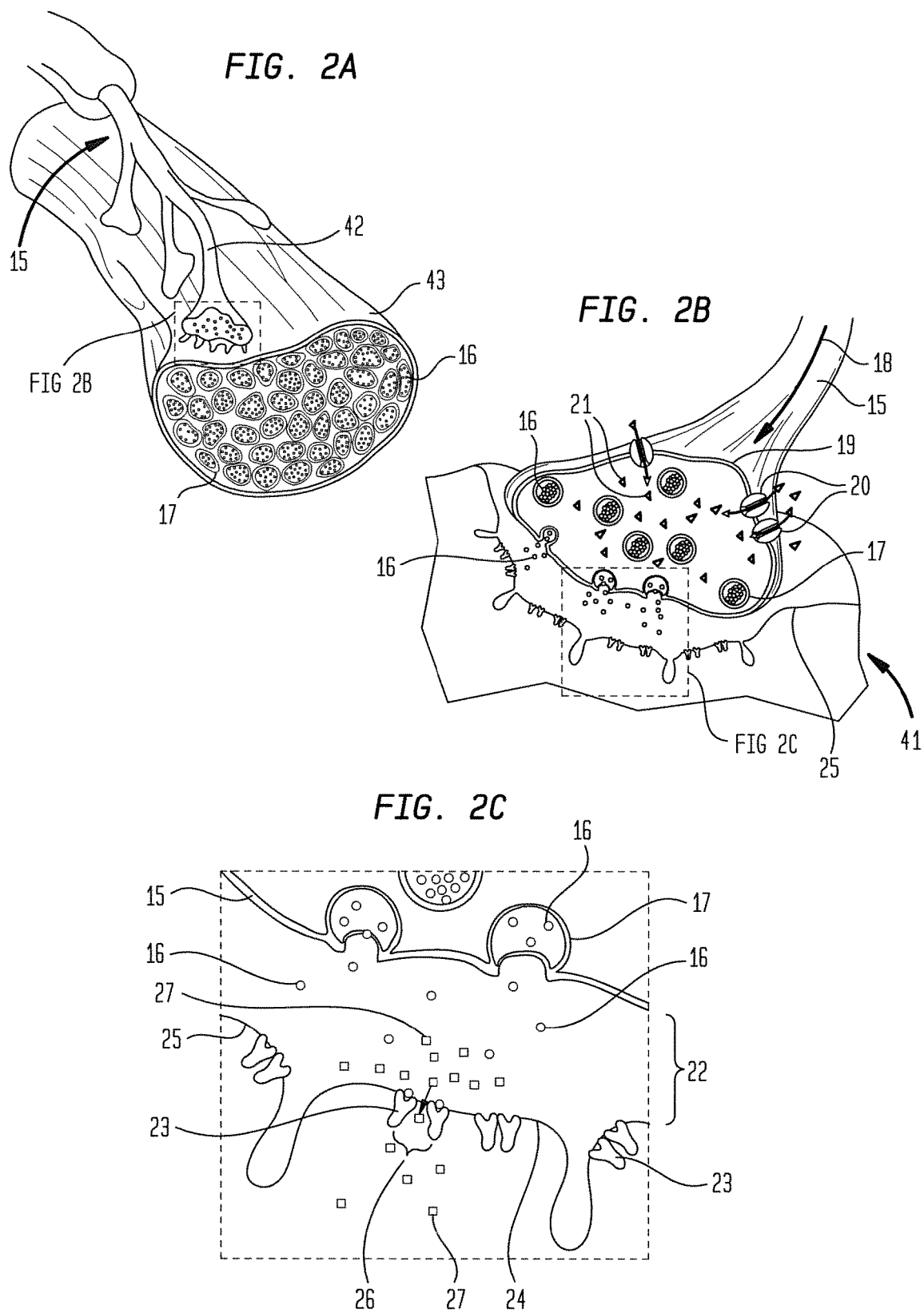
FIG. 2A shows an exemplary neuromuscular transmission cascade that can be modulated by methods of the inventive physical therapy system.
FIG. 2B shows an exemplary neuromuscular transmission cascade that can be modulated by methods of the inventive physical therapy system.
FIG. 2C shows an exemplary neuromuscular transmission cascade that can be modulated by methods of the inventive physical therapy system.
Figure 3:
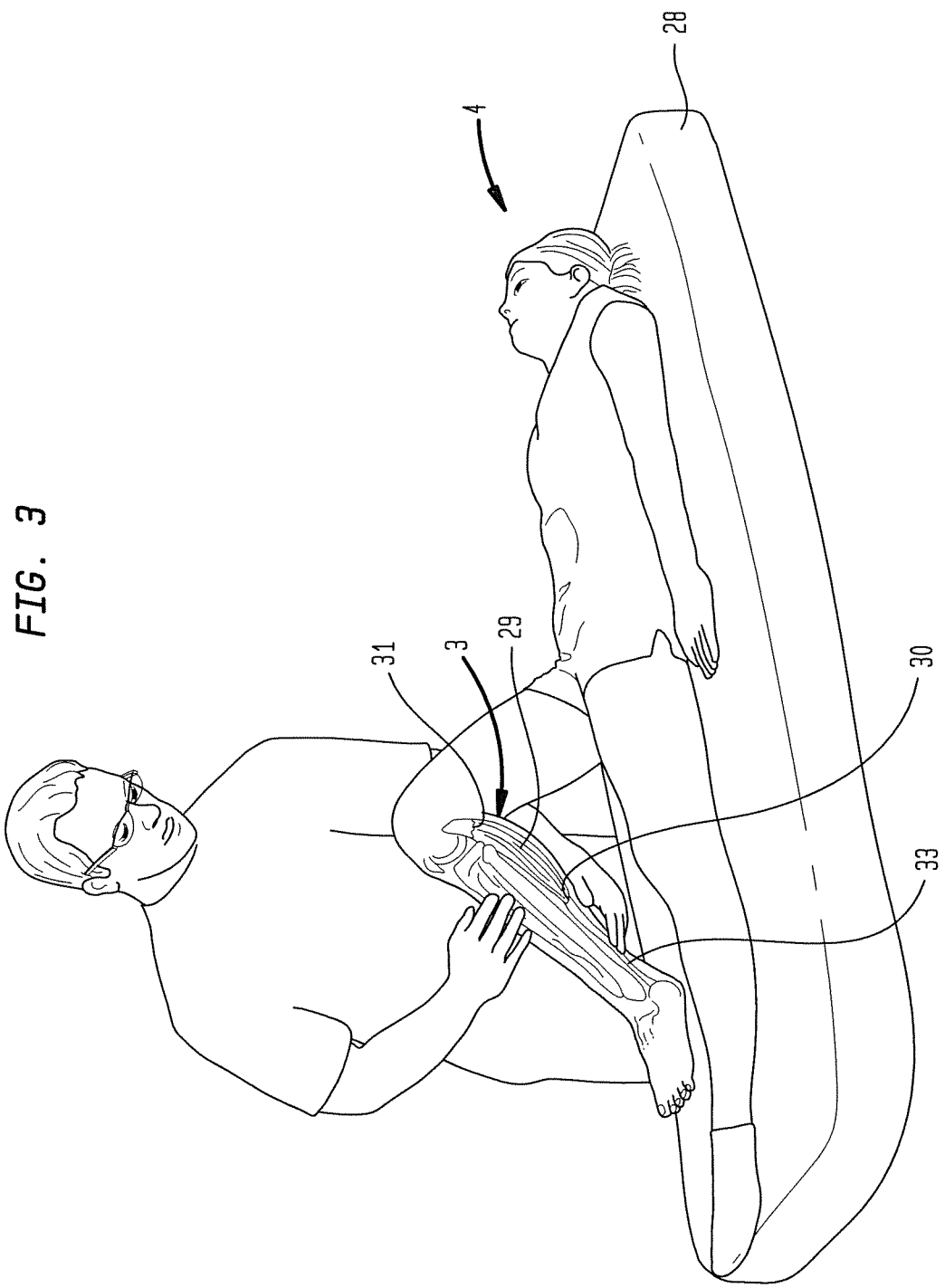
FIG. 3 shows an exemplary method of using a particular embodiment of the inventive physical therapy system.

Now referring primarily to FIG. 1, embodiments of the inventive method can include one or more of: locating a target muscle (5), locating a target muscle end, locating a target muscle location (7) a distance from the target muscle end (9), and providing a stimulus (10) to the target muscle location (11), the stimulus (12) operable to increase muscle control (13) or decrease neuromuscular inhibition (14) of the target muscle (3).

The term "target muscle" for the purposes of this invention means any band or bundle of fibrous tissue in a human or animal body that has the ability to contract.

The term "neuromuscular inhibition" for the purposes of this invention means an incomplete or complete inhibition of neuromuscular transmission.

The term "neuromuscular transmission" for the purposes of this invention means an event occurring at a neuromuscular junction including the transmission of a neurotransmitter from an end of a neuron to a receptor on a muscle.

The term "muscle control" for the purposes of this invention means the ability to contract one or more muscles.

Now referring primarily to FIG. 2A, FIG. 2B, and FIG. 2C, which generally illustrate neuromuscular transmission, a neuron (15) can synthesize neurotransmitters (16) (for example, acetylcholine) and can store the neurotransmitters (16) in synaptic vesicles (17). Arrival of an action potential (18) at the synaptic end bulb (19) can function to open voltage-gated calcium ion ($Ca^{2+}$) channels (20), which can result in a subsequent increase in the concentration of intracellular $Ca^{2+}$ (21). This increased intracellular $Ca^{2+}$ (21) concentration can trigger a cascade of signaling events operable to facilitate migration of the neurotransmitter-containing synaptic vesicles (17) to the periphery of the synaptic end bulb (16) of the neuron (15), where the neurotransmitter-containing synaptic vesicles (17) can rupture and release the neurotransmitters (16) into the synaptic cleft (22). The neurotransmitters (16) can bind to neurotransmitter receptors (23) located on the motor endplate (24) of a myocyte (25), consequently activating the neurotransmitter receptors (23), which can respond by opening voltage-gated sodium ion ($Na^+$) channels (26), allowing an influx of $Na^+$ (27) into the myocyte (25). The $Na^+$ (27) influx can depolarize the motor endplate (24), which can generate and propagate an action potential (18), leading to muscle contraction.

Now referring generally to FIG. 3 through FIG. 10, with respect to locating a target muscle (5) within the body of a subject (4), the subject (4) can be positioned on a support surface (28) to provide access to the target muscle (3) (as shown in the examples of FIG. 3, FIG. 4, FIG. 7, and FIG. 9). The position of the subject (4) useful in various embodiments of the inventive method can vary depending upon the specific target muscle (3) and as illustrative examples, can include: standing, sitting, long-sitting, squatting, lying (supine or prone), side-lying, kneeling, crouching, static crawling, or the like, or combinations thereof.

The target muscle (3) can be located by visualization, palpation, or the like, or combinations thereof; however, this description is not intended to limit locating the target muscle (5) solely to these procedures. Visualization of a target muscle (3) can be accomplished by an eye whether assisted or unassisted by optics. Visualization of a target muscle (3) can be facilitated by having a subject (4) lengthen and contract the target muscle (3) one or a plurality of times, thereby distinguishing the target muscle (3) from the surrounding tissue. Additionally, target muscle (3) visualization can be accomplished by medical imaging, including as illustrative examples, techniques such as radiology, which can use imaging technologies including X-ray radiography, magnetic resonance imaging, medical ultrasonography or ultrasound, endoscopy, elastography, tactile imaging, thermography, medical photography, nuclear medicine functional imaging techniques, 3-D motion-capture imaging, or the like, or combinations thereof.

As to particular embodiments, palpation can be used to locate a target muscle (3). Palpation can include manual palpation, which can be an examination by touch, an act of touching, feel, or an act of feeling of a surface of a subject (4) to determine a location or a condition of a portion of the subject (4) beneath the surface of the subject (4), such as a target muscle (3). In addition, palpation can include virtual palpation, for example haptic palpation. Palpation of a target muscle (3) can be facilitated by having a subject (4) lengthen and contract the target muscle (3) one or a plurality of times, thereby distinguishing the target muscle (3) from the surrounding tissue.

Figure 4:
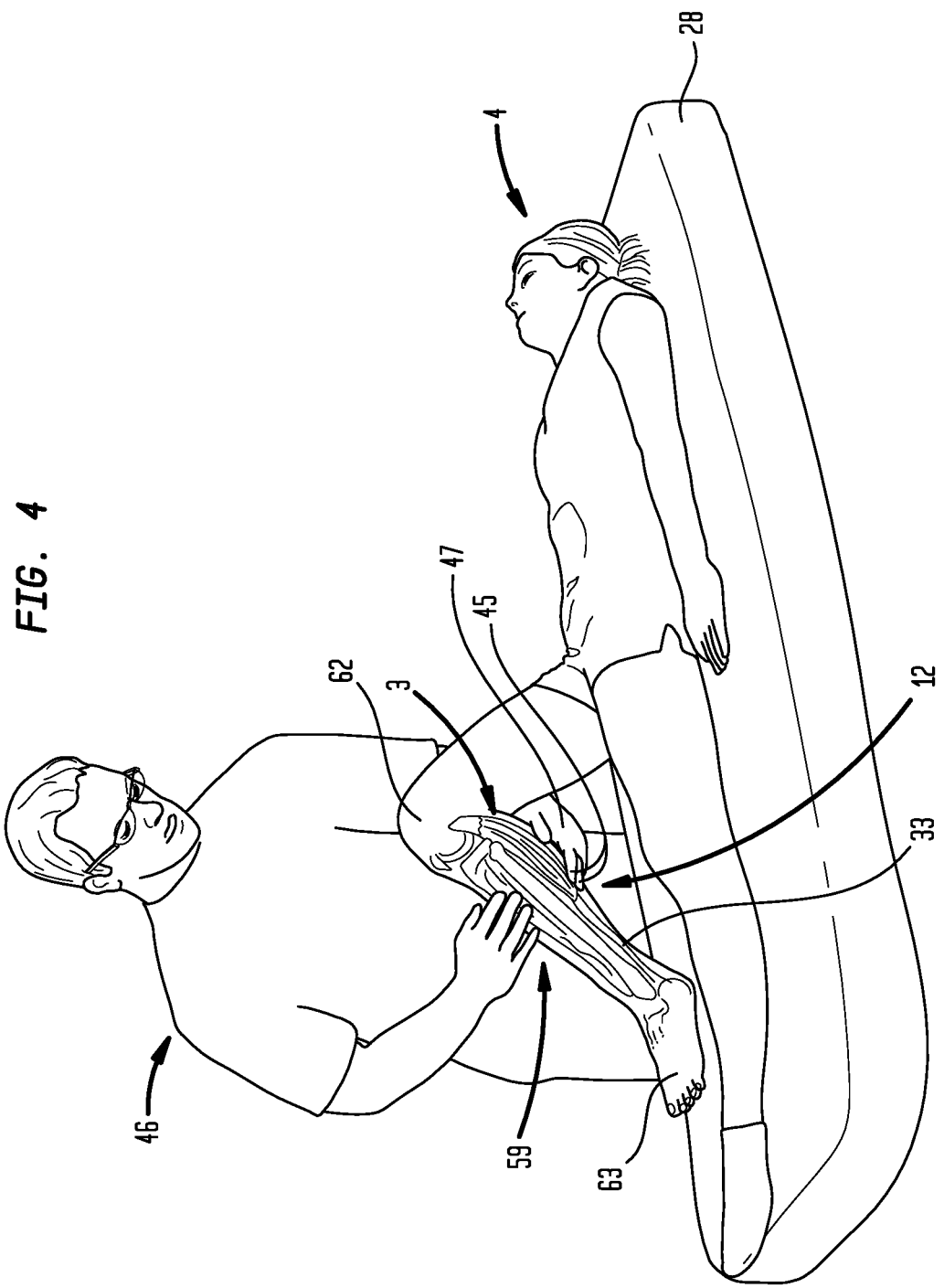
FIG. 4 shows an exemplary method of using a particular embodiment of the inventive physical therapy system.
Figure 5:
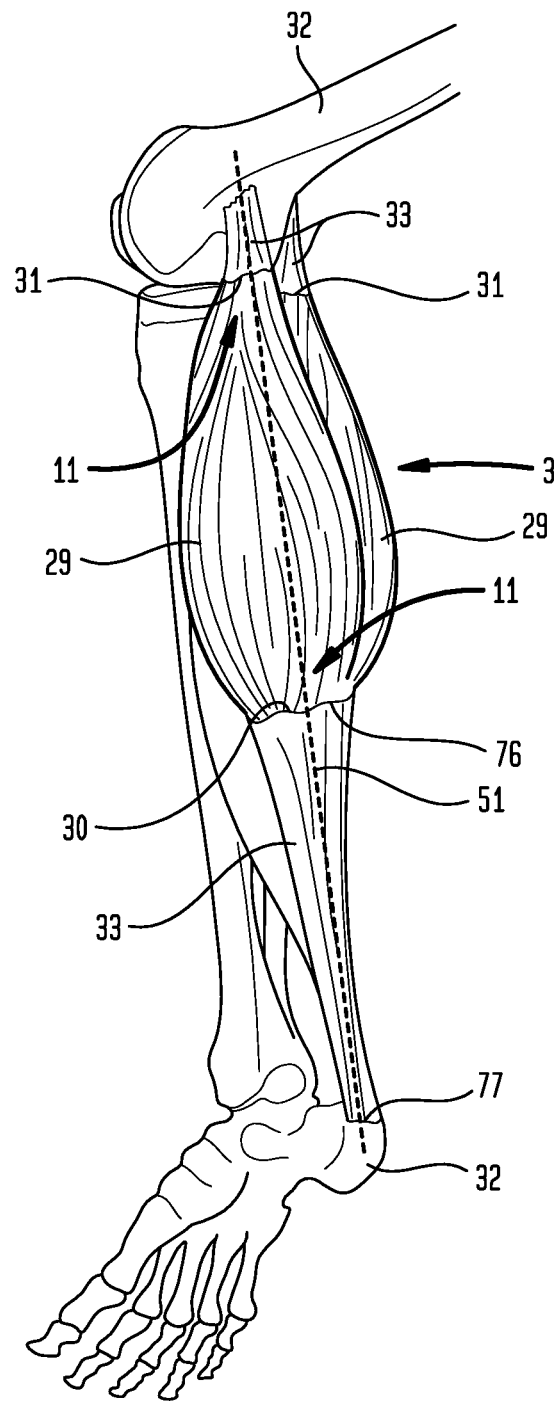
FIG. 5 shows exemplary elements of a method included in a particular embodiment of the inventive physical therapy system.
Figure 6:
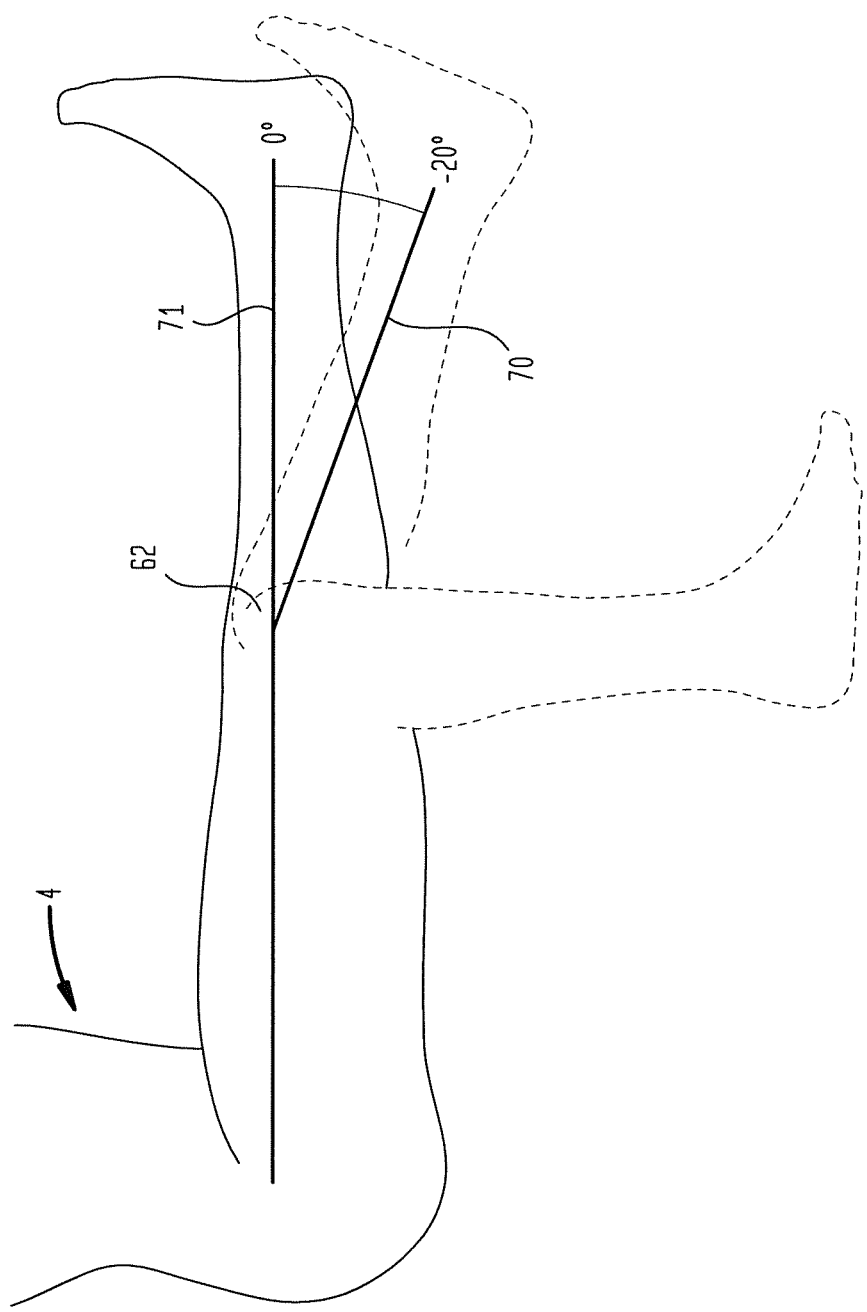
FIG. 6 shows an exemplary measureable result of a method included in a particular embodiment of the inventive physical therapy system.
Figure 7:
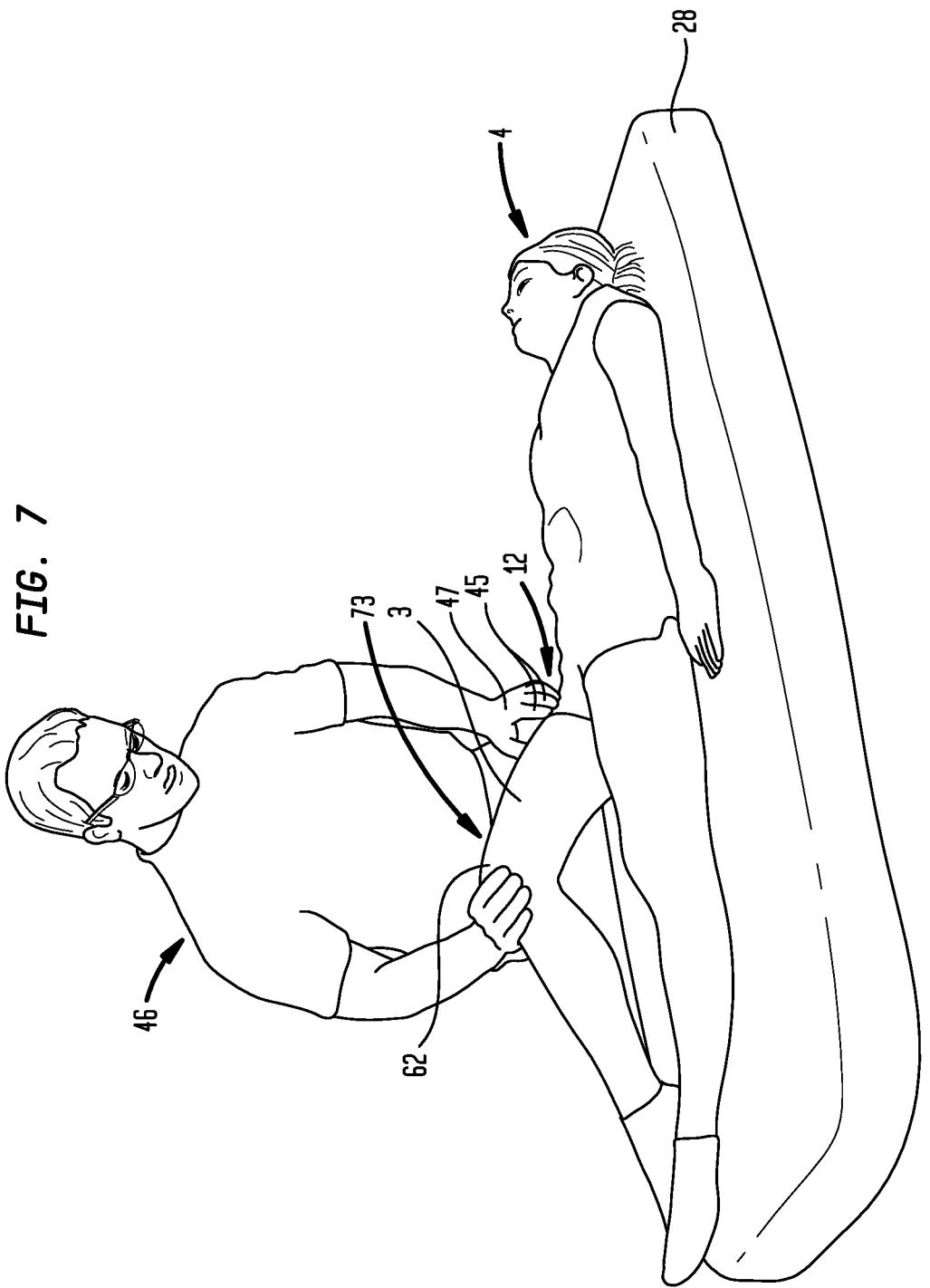
FIG. 7 shows an exemplary method of using a particular embodiment of the inventive physical therapy system.
Figure 8:
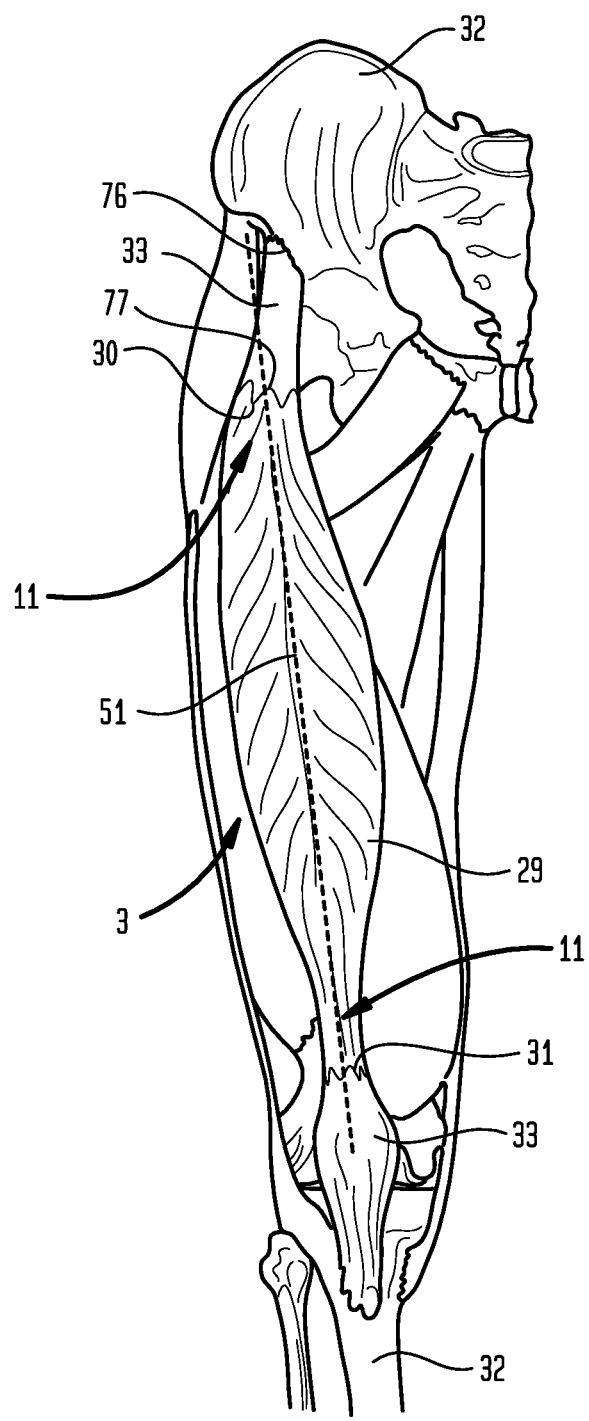
FIG. 8 shows exemplary elements of a method included in a particular embodiment of the inventive physical therapy system.
Figure 9:
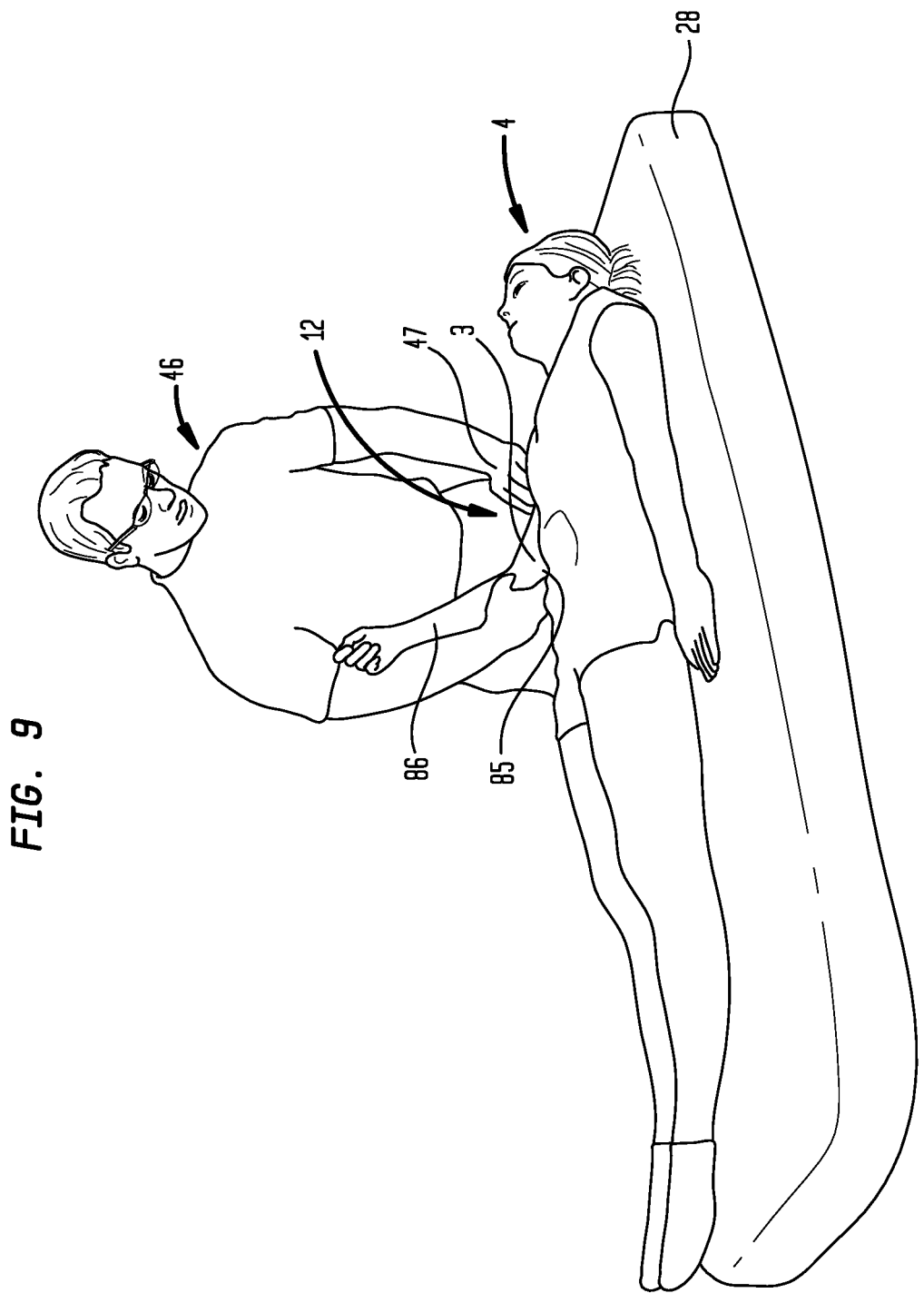
FIG. 9 shows an exemplary method of using a particular embodiment of the inventive physical therapy system.
Figure 10:
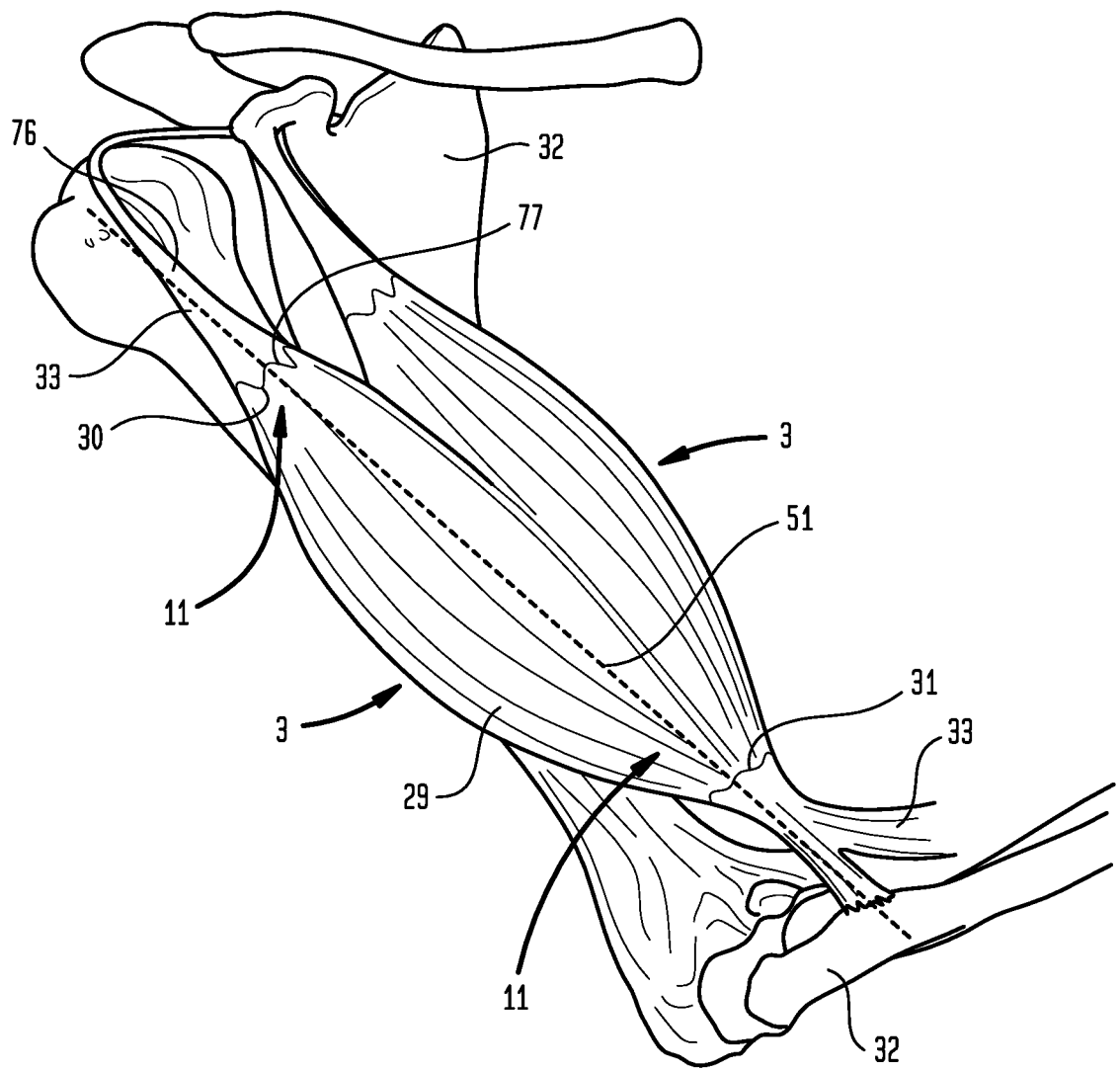
FIG. 10 shows exemplary elements of a method included in a particular embodiment of the inventive physical therapy system.

Again referring generally to FIG. 3 through FIG. 10, the inventive method can further include locating a target muscle end. A target muscle (3) can include a target muscle belly (29) longitudinally disposed between a target muscle first end (30) and a target muscle second end (31). Each target muscle end (30)(31) can be correspondingly joined to a bone (32) by a tendon (33) (as shown in the examples of FIG. 5, FIG. 8, and FIG. 10).

Again referring primarily to FIG. 3 through FIG. 10, the inventive method can further include locating a target muscle location (7) on the target muscle (3) (or "a target muscle first location" and "a target muscle second location" and so forth) which can act, when stimulated, to increase muscle control (13) or decrease neuromuscular inhibition (14) of the target muscle (3) of a subject (4).

As to particular embodiments, a target muscle first location can be located a first distance from the target muscle first end (30). The first distance from the target muscle first end (30) can be in a range of between about 0.5 inches to about 6 inches. The first distance can be one or more of the distances selected from the group including or consisting of: between about 0.5 inches to about 1.5 inches, between about 1.0 inch to about 2.0 inches, between about 1.5 inches to about 2.5 inches, between about 2.0 inches to about 3.0 inches, between about 2.5 inches to about 3.5 inches, between about 3.0 inches to about 4.0 inches, between about 3.5 inches to about 4.5 inches, between about 4.0 inches to about 5.0 inches, between about 4.5 inches to about 5.5 inches, and between about 5.0 inches to about 6.0 inches. As an illustrative example, the first distance can be about one inch from the target muscle first end (30).

As to particular embodiments, a target muscle second location can be located a second distance from the target muscle second end (31). The second distance from the target muscle second end (31) can be in a range of between about 0.5 inches to about 6 inches. The second distance can be one or more of the distances selected from the group including or consisting of: between about 0.5 inches to about 1.5 inches, between about 1.0 inch to about 2.0 inches, between about 1.5 inches to about 2.5 inches, between about 2.0 inches to about 3.0 inches, between about 2.5 inches to about 3.5 inches, between about 3.0 inches to about 4.0 inches, between about 3.5 inches to about 4.5 inches, between about 4.0 inches to about 5.0 inches, between about 4.5 inches to about 5.5 inches, and between about 5.0 inches to about 6.0 inches. As an illustrative example, the second distance can be about one inch from the target muscle second end (31).

As to particular embodiments, the target muscle location (11) can be distinguished as a discrete location from the surrounding locations on the target muscle (3) because when stimulated, the target muscle location (11) can act to increase muscle control (13) of the target muscle (3) of the subject (4) or can act to decrease neuromuscular inhibition (14) of the target muscle (3) of the subject (4). Typically, the target muscle location (11) will be discrete from the target muscle ends (30)(31), which generally comprise the origin of the target muscle (3) and the insertion of the target muscle (3). Both the origin and insertion of the target muscle (3) can include a Golgi Tendon Organ, which may not be associated with increased muscle control (13) of the target muscle (3) or neuromuscular transmission. Thus, stimulation provided to the origin or insertion of the target muscle (3) may not increase muscle control (13) or decrease neuromuscular inhibition (14) of the target muscle (3).

Additionally, the target muscle location (11) can be distinguished as a limited area or volume within a portion of the target muscle belly (29) which can be stimulated to increase muscle control (13) or decrease neuromuscular inhibition (14) in contrast to conventional methods that include general manipulation, massage or stimulation of the target muscle belly (29) to relax the target muscle (3). For example, a target muscle location (11) of the inventive method can be discretely limited to a target muscle location area that includes a target muscle location area of between about 0.1% to about 5% of the area of target muscle belly (29). The target muscle location area can be a pre-determined discrete target muscle location (11), which without stimulation of a greater area of the target muscle belly (29), can upon stimulation act to increase muscle control (13) of the target muscle (3) of the subject (4) or decrease neuromuscular inhibition (14) of the target muscle (3) of the subject (4).

By way of contrast, conventional methods include general manipulation, massage, or stimulation of an area of the target muscle belly (29) much greater than 0.1% to about 5% of the area of the target muscle belly (29), for example, up to the entire manipulable surface area of the target muscle belly (29).

Now referring primarily to FIG. 2A, FIG. 2B, and FIG. 2C, the target muscle location (11) of the inventive method can be associated with a neuromuscular junction and locating the target muscle location (7) can include locating a target muscle location (7) in association with a neuromuscular junction. Generally, a neuromuscular junction can include a synapse (41) disposed between an efferent nerve fiber (42) and a muscle fiber (43) (as shown in the examples of FIG. 2A, FIG. 2B, and FIG. 2C). As described above, an action potential (18) can be transmitted from an efferent nerve fiber (42) to a muscle fiber (43), causing a cascade that can result in muscle contraction. As a neuromuscular junction can be involved with neuromuscular transmission, stimulation provided to the neuromuscular junction can modulate neuromuscular inhibition, for example by decreasing neuromuscular inhibition (14). Consequently, particular embodiments of the inventive method can further include locating a target muscle location (7) associated with a neuromuscular junction.

Now referring generally to FIG. 3 through FIG. 10, the inventive method can further include providing a stimulus (10) to a target muscle location (11). As illustrative examples, a stimulus (12) suitable for use with the inventive method can include one or more of: mechanical stimulus, electrical stimulus, pharmacological stimulus, or the like, or combinations thereof.

As to particular embodiments a stimulus (12) can include an amount of pressure and providing a stimulus to a target muscle location (10) can include applying an amount of pressure to a target muscle location (10A). The amount of pressure can be delivered to a target muscle location (11) by one or more fingertips (45) of a provider (46) (as shown in the examples of FIG. 4, FIG. 7, and FIG. 9); however, an amount of pressure can be delivered to a target muscle location (11) by one or more various suitable pressure-generating members (47), including elements of a hand such as a finger, a knuckle, a palm, a heel, or mechanical members having a configuration suitable for delivering an amount of pressure to a target muscle location (11), or the like, or combinations thereof.

As to particular embodiments, the amount of pressure can be delivered to a target muscle location (11) discrete from delivery of an amount of pressure to the remaining target muscle belly (29). Accordingly, as to particular embodiments, the pressure-generating member (47) can be configured based upon the target muscle location area which can be lesser or greater depending upon target muscle (3). For example, the amount of pressure can be applied by one fingertip (45) to a target muscle location (11) of corresponding lesser target muscle location area while the amount of pressure can be delivered by a plurality of fingertips (45) to a target muscle location (11) of correspondingly greater target muscle location area.

Now referring primarily to FIG. 5, FIG. 8, and FIG. 10, as to particular embodiments, the target muscle location (11) can include a target muscle location area greater than the area engaged by the pressure-generating member (47). Accordingly, the pressure-generating member (47) can be repeatedly engaged with the target muscle location (11) along a target muscle location latitudinal axis or a target muscle location longitudinal axis (51).

As one illustrative example, the pressure-generating member (47) can be positioned such that a pressure-generating member longitudinal axis can be substantially perpendicular to the target muscle location longitudinal axis (51) to deliver the amount of pressure along the pressure-generating member longitudinal axis in substantially perpendicular relation to the target muscle belly longitudinal axis (51).

The amount of pressure can be selected from the group including or consisting of: an amount of invariant continuous pressure, an amount of substantially invariant continuous pressure, an amount of variant pressure, or combinations thereof. For example, substantially invariant continuous pressure can be delivered by engagement of the pressure-generating member (47) with the target muscle location (11) as substantially constant maximum pressure amplitude over the period of delivery time and variant pressure can be delivered by engagement of the pressure-generating member (47) with the target muscle location (11) as substantially inconstant maximum pressure amplitude over the period of delivery time (for example, a pulsatile pressure delivery).

As to particular embodiments, the amount of pressure delivered can be an amount of pressure (whether delivered as an invariant pressure or a variant pressure) which increases muscle control (13) of the target muscle (3) or an amount of pressure which decreases neuromuscular inhibition (14) of the target muscle (3). The amount of pressure delivered to a target muscle location (11) can be lesser or greater depending upon the target muscle (3), the target muscle location (11), the degree of loss of muscle control or degree of neuromuscular inhibition, or combinations thereof. For example, a lesser amount of pressure can be delivered to increase muscle control (13) or decrease neuromuscular inhibition (14) in a target muscle (3) having a target muscle location (11) proximate the superficial anatomy of the subject (4), such as a gastrocnemius muscle. Alternatively, a greater amount of pressure can be delivered to increase muscle control (13) or decrease neuromuscular inhibition (14) in a target muscle (3) having a target muscle location (11) distal from the superficial anatomy of the subject (4), such as a soleus muscle.

As to particular embodiments, the amount of pressure delivered by the pressure-generating member (47) can depress the target muscle belly (29) at the target muscle location (11) a distance which acts to increase muscle control (13) of the target muscle (3). Accordingly, applying an amount of pressure to a target muscle location (10A) can include depressing a portion of a muscle belly at a target muscle location (10B). As to particular embodiments, the amount of pressure delivered to the target muscle location (11) can decrease neuromuscular inhibition (14) of the target muscle (3). Consequently, the amount of pressure can act to increase neuromuscular transmission, likely by modulating one or more components of the neuromuscular transmission cascade. The list of components of the neuromuscular transmission cascade described above is not comprehensive. As such, the amount of pressure delivered can modulate one or more of the components described above as well as additional components of the neuromuscular transmission cascade omitted from the above description. As an illustrative example, the amount of pressure can act to stimulate release of neurotransmitters (16) from the synaptic end bulb (19) into the synaptic cleft (22).

Embodiments can further include delivery of the amount of pressure over a time period. As to particular embodiments, applying an amount of pressure to a target muscle location (10A) can include depressing a portion of a muscle belly at a target muscle location for a time period (10C). The time period can range from between about one second to about twenty seconds. The time period can be selected from the group including or consisting of: between about 1 second and about 3 seconds, between about 2 seconds and about 4 seconds, between about 3 seconds and about 5 seconds, between about 4 seconds and about 6 seconds, between about 5 seconds and about 7 seconds, between about 6 seconds and about 8 seconds, between about 7 seconds and about 9 seconds, between about 8 seconds and about 10 seconds, between about 9 seconds and about 11 seconds, between about 10 seconds and about 12 seconds, between about 11 seconds and about 13 seconds, between about 12 seconds and about 14 seconds, between about 13 seconds and about 15 seconds, between about 14 seconds and about 16 seconds, between about 15 seconds and about 17 seconds, between about 16 seconds and about 18 seconds, between about 17 seconds and about 19 seconds, and between about 18 seconds and about 20 seconds.

As an illustrative example, an amount of pressure can be delivered to the target muscle location (11) as an amount of pressure having a constant maximum amplitude of about two seconds. As another illustrative example, the amount of pressure can be delivered to the target muscle location (11) as an amount of pressure having an inconstant maximum amplitude of pulsatile form incorporating five pulses, each pulse of about two seconds.

Now referring primarily to FIG. 12, as to particular embodiments, the inventive method can further include locating a target muscle second end (53), locating a target muscle second location (54) a second distance from the target muscle second end (53), and providing a second stimulus (56) to the target muscle second location (54), each as above described for the corresponding method of locating a first target muscle first end, locating a target muscle first location (7), and providing a first stimulus (10) to the target muscle first location (7).

As to particular embodiments, providing a first stimulus (10) to a target muscle first location (7) and providing a second stimulus (56) to a target muscle second location (54) can be delivered, as above described, either concurrently or serially to increase muscle control (13) or decrease neuromuscular inhibition (14).

Now referring primarily to FIG. 13, as to particular embodiments of the inventive physical therapy method (1), the inventive method can further include a functional screen (57), which can identify biomechanical deficiencies of a subject (4). A functional screen (57) can comprise an assessment of a subject (4), including a weight-bearing assessment, an active assessment, a multiplanar assessment, a total body assessment, or the like, or combinations thereof. Additionally, a functional screen (57) can comprise an assessment of actions of a subject (4), including actions that mimic Activities of Daily Living, actions that mimic sport activities, actions that mimic work activities, or the like, or combinations thereof. Biomechanical deficiencies of a subject (4) identified by the functional screen (57) can facilitate in locating a target muscle (5) by directing a provider (46) toward a target muscle (3) associated with a particular biomechanical deficiency.

Again referring primarily to FIG. 13, as to particular embodiments, the inventive method can further include testing neuromuscular facilitation (58), which can assess the ability of a target muscle (3) to contract as a result of communication with the nervous system. As to particular embodiments, testing neuromuscular facilitation (58) can include positioning a target muscle (58A) between a midrange of motion and a shortened range of motion. As to other particular embodiments, testing neuromuscular facilitation (58) can include measuring a neuromuscular response (58B) of the target muscle (3) positioned between a midrange of motion and a shorted range of motion to a neuromuscular facilitation test stimulus. As to yet other particular embodiments, testing neuromuscular facilitation (58) can include scoring the neuromuscular response (58C) of the target muscle (3) positioned between a midrange of motion and a shorted range of motion to the neuromuscular facilitation test stimulus based on a binary determination of whether the target muscle (3) contracts in response to the neuromuscular facilitation test stimulus or the target muscle (3) does not contract in response to the neuromuscular facilitation test stimulus. As to still yet other particular embodiments, the inventive physical therapy method (1) can include providing a first stimulus (10) to the target muscle (3) which does not contract in response to the neuromuscular facilitation test stimulus.

Again referring primarily to FIG. 13, as to particular embodiments, the inventive method can further include repeating: positioning the target muscle (58A), measuring the neuromuscular response (58B) of the target muscle (3), scoring the neuromuscular response (58C) of the target muscle (3), and providing the first stimulus (10) to the target muscle (3) until the target muscle (3) contracts in response to the neuromuscular facilitation test stimulus.

Example 1

Now referring primarily to FIG. 3 through FIG. 6 which show a first illustrative example of the inventive method of increasing muscle control (13) or decreasing neuromuscular inhibition (14) of the gastrocnemius muscle.

Now referring primarily to FIG. 5, the gastrocnemius muscle, a posterior muscle of the calf of the lower leg (59) has a lateral head which originates from the lateral condyle of the femur, while the gastrocnemius muscle medial head originates from the medial condyle of the femur. The opposing end of the gastrocnemius muscle couples to the Achilles tendon, which inserts into the posterior surface of the heel bone. Actions of the gastrocnemius muscle can pull the heel upward and correspondingly extend the foot downward. Actions of the gastrocnemius muscle can also pull the lower leg (11) towards the posterior upper leg (73), causing knee joint (62) flexion. Accordingly, the gastrocnemius muscle can be involved with movements including standing, walking, running, jumping, or the like, or combinations thereof.

The subject (4) was positioned on a support surface (28) to allow access to the gastrocnemius muscle in the posterior lower leg (59). In the instant example, the subject (4) was positioned in a supine position, the leg including the gastrocnemius muscle flexed at the knee joint (62) with the foot (63) resting flat on the support surface (28) such that the foot (63) was in a plantar flexed position.

The gastrocnemius muscle within the lower leg (59) of the subject (4) was located by manually palpating the Achilles tendon along a substantially longitudinal axis from the Achilles tendon distal end toward the Achilles tendon proximal end. Once the Achilles tendon proximal end was located, the gastrocnemius muscle distal first end was located adjacent to the Achilles tendon proximal end.

The gastrocnemius muscle first location was located a first distance from the gastrocnemius muscle distal first end by manually palpating the gastrocnemius muscle along a substantially longitudinal axis (51) from the gastrocnemius muscle distal first end toward the gastrocnemius muscle proximal second end, moving a first distance of about one inch to a discrete gastrocnemius muscle first location within a portion of the gastrocnemius muscle belly associated with a neuromuscular junction.

Once the gastrocnemius muscle first location was located, a first stimulus (12) was delivered to the gastrocnemius muscle at the gastrocnemius muscle first location in the form of an amount of pressure applied by one or more fingertips (45) of the provider (46). The amount of pressure delivered to the gastrocnemius muscle first location was adjusted until there was a measurable increase in the output force or range of motion about the knee joint (62) of the subject (4).

Now referring primarily to FIG. 6, the range of motion about the knee joint (62) of the subject (4) prior to administration of the inventive method was measured at about −20 degrees of knee extension (70). Administration of the inventive method, as above described, resulted in a range of motion about the knee joint (62) of about 0 degrees of knee extension (71). Accordingly, administration of the inventive method resulted in a 20 degree increase in range of motion about the knee joint (62) of the subject (4).

Example 2

Now referring primarily to FIG. 7 and FIG. 8, the inventive method was administered to the rectus femoris muscle of a subject (4).

The rectus femoris muscle, an anterior muscle of the upper leg (73), has a straight head originating from the anterior inferior iliac spine and the reflected head originating from the ilium above the acetabulum. The opposing end of the rectus femoris muscle inserts into the patella, or knee cap, via the quadriceps tendon. Actions of the rectus femoris muscle can include flexing the thigh at the hip joint and extending the lower leg at the knee joint.

The subject (4) was positioned on a support surface (28) in a supine position, the leg including the rectus femoris muscle bolstered at the knee joint (62) allowing access to the rectus femoris muscle in the anterior upper leg (73).

The rectus femoris muscle within the upper leg (73) of the subject (4) was located by manually palpating the tendon (33) coupling the rectus femoris muscle proximal first end with the anterior inferior iliac spine along a substantially longitudinal axis (51) from the tendon proximal end (76) toward the tendon distal end (77). Once the tendon distal end (77) was located, the rectus femoris muscle proximal first end can be located adjacent to the tendon distal end (77).

A rectus femoris muscle first location was located a first distance from the rectus femoris muscle proximal first end by manually palpating the rectus femoris muscle along a substantially longitudinal axis (51) from the rectus femoris muscle proximal first end toward the rectus femoris muscle distal second end, moving a first distance of about one inch to a discrete rectus femoris muscle first location within a portion of the rectus femoris muscle associated with a neuromuscular junction.

Upon locating the rectus femoris muscle first location, the inventive method further included providing a first stimulus (10) to the rectus femoris muscle at the rectus femoris muscle first location, the first stimulus (12) including an amount of pressure applied by one or more fingertips (45) of the provider (46) until an increase in muscle control of the rectus femoris muscle was observed in the subject (4). As to particular embodiments, the increase in muscle control of the rectus femoris muscle can be assessed by testing rectus femoris muscle neuromuscular facilitation.

Example 3

Now referring primarily to FIG. 9 through FIG. 10, the inventive method was applied to the biceps brachii muscle of a subject (4).

Now referring primarily to FIG. 10, the biceps brachii muscle, a two-headed anterior muscle of the upper arm includes a long head which originates from the supraglenoid tubercle and a short head which originates from the coracoid process of the scapula. The opposing end of the biceps brachii muscle inserts into the radial tuberosity. Actions of the biceps brachii muscle include flexing the elbow (85) and supinating the forearm (86).

The subject (4) was positioned in a supine position on a support surface (28) with the arm including the biceps brachii muscle flexed at the elbow (85) to allow access to the biceps brachii muscle in the anterior upper arm of the subject (4).

The long head of the biceps brachii muscle within the upper arm of the subject (4) was located by manually palpating the tendon coupling the long head of the biceps brachii proximal first end with the supraglenoid tubercle along a substantially longitudinal axis (51) from the tendon proximal end toward the tendon distal end. Once the tendon distal end was located, the long head of the biceps brachii proximal first end was located adjacent to the tendon distal end.

The long head of the biceps brachii muscle first location was located a first distance from the long head of the biceps brachii muscle proximal first end by manually palpating the long head of the biceps brachii muscle along a substantially longitudinal axis (51) from the long head of the biceps brachii muscle proximal first end toward the long head of the biceps brachii muscle distal second end, moving a first distance of about one inch to a discrete long head of the biceps brachii muscle first location within a portion of the long head of the biceps brachii muscle belly associated with a neuromuscular junction.

Once the long head of the biceps brachii muscle first location was located, a first stimulus (12) was delivered to the long head of the biceps brachii muscle at the long head of the biceps brachii muscle first location in the form of an amount of pressure delivered as five pulses each over a time period of about two seconds, which resulted in a measured increase in the muscle control of the biceps brachii muscle of the subject (4).

As a second illustrative example, the range of motion about the shoulder joint (93) of a subject (4) prior to administration of the inventive method can be measured at about 120 degrees of shoulder flexion (94). Administration of the inventive method, as above described, can result in about 180 degrees of shoulder flexion (95). Accordingly, administration of the inventive method can result in a 60 degree increase in range of motion about the shoulder joint (93) of the subject (4).

Example 4

Now referring primarily FIG. 11 and Table 1, the inventive method can result in an increase in output force (96) of a target muscle (3) of a subject (4). In an experiment, twenty-two subjects (97) having decreased muscle control or neuromuscular inhibition of a rectus femoris muscle were tested. Rectus femoris muscle output force (96) was assessed using a dynamometer both before administration of the inventive method and after administration of the inventive method.

Now referring to Table 1, each subject (4) was given a numerical identifier as shown in column one. The rectus femoris muscle output force (96) of each subject (4) prior to administration of the inventive method was recorded in column two as pounds of pressure. The rectus femoris muscle output force (96) after administration of the inventive method was recorded in column three as pounds of pressure. The percent increase (98) in output force (96) following administration of the inventive method (22) to each subject (4) was calculated and recorded in column four.

TABLE 1

| Subject Number | Output Force Before | Output Force After | Percent Increase |
| --- | --- | --- | --- |
| 1 | 24.0 | 27.0 | 12.5 |
| 2 | 26.6 | 29.6 | 11.3 |
| 3 | 26.5 | 27.1 | 2.3 |
| 4 | 22.0 | 24.9 | 13.2 |
| 5 | 28.7 | 36.4 | 26.8 |
| 6 | 15.2 | 18.5 | 21.7 |
| 7 | 15.1 | 15.9 | 5.3 |
| 8 | 31.6 | 32.9 | 4.1 |
| 9 | 25.9 | 32.6 | 25.9 |
| 10 | 37.5 | 39.9 | 6.4 |
| 11 | 33.7 | 39.7 | 17.8 |
| 12 | 32.7 | 38.3 | 17.1 |
| 13 | 25.5 | 35.6 | 39.6 |
| 14 | 43.1 | 45.7 | 10.7 |
| 15 | 47.2 | 55.9 | 14.2 |
| 16 | 30.6 | 32.3 | 5.6 |
| 17 | 28.6 | 33.5 | 17.2 |
| 18 | 22.8 | 26.8 | 17.2 |
| 19 | 21.5 | 25.3 | 17.2 |

TABLE 1-continued

| Subject Number | Output Force Before | Output Force After | Percent Increase |
| --- | --- | --- | --- |
| 20 | 25.5 | 29.8 | 17.2 |
| 21 | 40.4 | 47.3 | 4.7 |
| 22 | 15.2 | 17.6 | 15.2 |

Now referring primarily to FIG. 11, the percent increase (98) in rectus femoris muscle output force (96) following administration of the inventive method was plotted as a bar graph with each subject (4) identified along the horizontal axis (99) and each corresponding percent increase (98) in rectus femoris muscle output force (96) shown along the vertical axis (100). Overall, the average percent increase (98) in rectus femoris muscle output force (96) following administration of the inventive method was 14.7%.

As to particular embodiments of the inventive physical therapy method (1), increasing muscle control (13) can include decreasing neuromuscular inhibition (14), increasing neuromuscular transmission of a target muscle (13A), stimulating contraction of a target muscle (13B), alleviating a symptom associated with loss of muscle control of a target muscle (13C), or the like, or combinations thereof As to particular embodiments of the inventive physical therapy method (1), an increase in muscle control (13) or a decrease in neuromuscular inhibition (14) can result in a measureable result. As such, the inventive physical therapy method (1) can include measuring the muscle control of the target muscle (3). As to particular embodiments, measuring the muscle control of the target muscle (3) can include measuring a range of motion of a body part associated with extension or contraction of the target muscle (3), measuring an output force of the target muscle (3), measuring a movement of a body part associated with extension or contraction of the target muscle (3), measuring a posture of a subject (4), the posture associated with extension or contraction of the target muscle (3), or the like, or combinations thereof.

As to particular embodiments of the inventive physical therapy method (1), an increase in muscle control (13) or a decrease in neuromuscular inhibition (14) can result in a measureable result including an achievement of a movement. For example, prior to providing methods included in the inventive physical therapy method (1) to a subject (4), the subject (4) may not be able to step off of a curb. However, after the methods included in the inventive physical therapy method (1) are provided, the subject (4) may be able to achieve the movement(s) sufficient to step off of a curb.

As to particular embodiments of the inventive physical therapy method (1), an increase in muscle control (13) or a decrease in neuromuscular inhibition (14) can result in a measureable result including an achievement of a posture. For example, prior to providing methods included in the inventive physical therapy method (1) to a subject (4), the subject (4) may not be able touch their toes with their fingertips while standing straight-legged. After the methods included in the inventive physical therapy method (1) are provided, the subject (4) may be able to touch their toes with their fingertips.

As to particular embodiments of the inventive physical therapy method (1), administration of the inventive method can result in an increase in muscle control (13) or a decrease in neuromuscular inhibition (14) in the target muscle (3) or in one or more muscles related to or unrelated to the target muscle (3). As to particular embodiments, the inventive physical therapy method (1) can effect tension in a muscle opposing the target muscle (3) via reciprocal inhibition.

As can be easily understood from the foregoing, the basic concepts of the present invention may be embodied in a variety of ways. The invention involves numerous and varied embodiments of the inventive physical therapy system and methods for using such inventive physical therapy systems, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "palpation" should be understood to encompass disclosure of the act of "palpating"—whether explicitly discussed or not—and, conversely, were there effectively disclosure of the act of "palpating", such a disclosure should be understood to encompass disclosure of a "palpation" and even a "means for palpating." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) the inventive physical therapy system herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method for treating a target muscle having weak muscle contraction output force, comprising:
   identifying said target muscle having said weak muscle contraction output force;
   measuring muscle contraction output force of said target muscle with a dynamometer prior to treatment of said target muscle;
   subsequent to measuring said muscle contraction output force of said target muscle, treating the target muscle with a treatment, comprising:
      identifying corresponding origin and attachment of said target muscle;
      applying a first amount of pressure to only a target muscle belly first end a distance from said origin of said target muscle along a target muscle belly longitudinal axis with a first pressure-generating member; and
      applying a second amount of pressure to only a target muscle belly second end a distance from said attachment of said target muscle along said target muscle belly longitudinal axis with a second pressure-generating member; and
   subsequent to treating said target muscle with said treatment, measuring said muscle contraction output force of said target muscle with said dynamometer,
      wherein said treatment to the target muscle results in an increase in said muscle contraction output force as measured with said dynamometer.

2. The method of claim 1, further comprising repeating application of said first and second amounts of pressure to corresponding said target muscle belly first and second ends until said muscle contraction output force of said target muscle increases as measured with said dynamometer.

3. The method of claim 1, wherein said treatment further comprises adjusting amount of said first amount of pressure to said target muscle belly first end a distance from said origin of said target muscle or adjusting amount said second amount of pressure to said target muscle belly first end a distance from said origin of said target muscle until said muscle contraction output force of said target muscle increases as measured with said dynamometer.

4. The method of claim 1, wherein said first amount of pressure applied prior to said second amounts of pressure.

5. The method of claim 1, further comprising functionally screening a subject prior to identifying said target muscle having said weak muscle contraction output force.

6. The method of claim 5, wherein said functionally screening comprises assessing a weight-bearing activity.

7. The method of claim 5, wherein said functionally screening comprises assessing an active activity.

8. The method of claim 5, wherein said functionally screening comprises assessing a multiplanar activity.

9. The method of claim 5, wherein said functionally screening comprises assessing a total body activity.

10. The method of claim 5, wherein said functionally screening comprises assessing actions that mimic activities of daily living of said subject.

11. The method of claim 5, wherein said functionally screening comprises assessing actions that mimic sport activities of said subject.

12. The method of claim 5, wherein said functionally screening comprises assessing actions that mimic work activities of said subject.

13. The method of claim 1, further comprising functionally screening a subject after the application of said first and second amounts of pressure to corresponding said target muscle belly first and second ends.

14. The method of claim 1, further comprising positioning said target muscle between a midrange of motion and a shortened range of motion to test neuromuscular facilitation.

15. The method of claim 1, further comprising simultaneously applying said first and second amounts of pressure to corresponding said target muscle belly first and second ends.

* * * * *